United States Patent [19]

Gordon

[11] 4,107,426

[45] Aug. 15, 1978

[54] PROCESS FOR TREATING CELLULOSE

[76] Inventor: Roy Gerald Gordon, 22 Highland St., Cambridge, Mass. 02138

[21] Appl. No.: 702,534

[22] Filed: Jul. 6, 1976

[51] Int. Cl.$^2$ .................... A61F 13/16; B32B 27/42
[52] U.S. Cl. ...................... 536/56; 8/115.5; 8/120; 68/5 A; 128/156; 128/284; 128/290 P; 229/3.1; 536/82; 536/87; 536/88; 536/89
[58] Field of Search ............ 536/56, 82, 87, 88, 536/89; 128/290 P, 284, 156; 229/3.1; 8/115.5, 120

[56] References Cited

U.S. PATENT DOCUMENTS

| | | | |
|---|---|---|---|
| 2,512,195 | 6/1950 | Bener | 8/116.4 |
| 2,891,946 | 6/1959 | Volberg et al. | 536/82 |
| 2,992,214 | 7/1961 | Mench et al. | 536/82 |
| 3,089,493 | 5/1963 | Galindo | 128/283 |
| 3,137,540 | 6/1964 | Osugi et al. | 260/73 L |
| 3,626,943 | 12/1971 | Worcester | 128/286 |
| 3,705,146 | 12/1972 | Smith | 536/56 |
| 3,799,167 | 3/1974 | Miller et al. | 128/287 |
| 3,934,587 | 1/1976 | Gordon | 128/284 |
| 3,966,484 | 6/1976 | Helmer et al. | 536/56 |

*Primary Examiner*—Ronald W. Griffin
*Attorney, Agent, or Firm*—Thompson, Birch, Gauthier & Samuels

[57] ABSTRACT

A water-repellent cellulose and articles comprising the water-repellent cellulose are disclosed together with a process and apparatus for preparing the same. The water-repellent cellulose is prepared by exposing one or more sides and edges of a cellulose sheet, pad, or cloth to aliphatic acid chloride vapors. The resulting product is water-repellent along the treated sides and edges and, in general, water-permeable along the untreated sides and edges. Therefore, the treated cellulose products of this invention are especially suitable for disposable articles of sanitary clothing, sanitary napkins, bandaging materials, paper cups, bags and the like.

29 Claims, 7 Drawing Figures

PROCESS FOR TREATING CELLULOSE

BACKGROUND OF THE INVENTION

This invention is directed to the problem of producing materials and articles which are water-repellent during use yet can be readily disposed of in an aqueous environment, such as by flushing in a toilet, after use is completed. Such materials are particularly desirable for the production of disposable articles of sanitary clothing, for example diapers, colostomy bags, sanitary napkins, etc., and for bandaging materials. In such applications, it is hygienically undesirable to store the used article with other refuse for commercial disposal. However, other important areas of application are disposable containers of all types, such as paper cups and paper bags, and various types of packaging, such as cardboard boxes and drums. In the latter applications where the need for on-the-spot disposibility is less acute, the property of being readily dispersed in aqueous enviivironments would still facilitate commercial disposal of the used products. Two general approaches to this problem have been employed in the past. One approach has been to use composite structures wherein one layer of material is waterproof and intended to be reused, for example a rubber sheet, while the second layer is water-disposable. It will be appreciated that such articles are cumbersome and, at best, partially disposable. A second approach has been to use various means for coating or impregnating a base material to impart water-repellent properties thereto. In the latter case, it has generally been found that when the amount of the coating or impregnating substance used is sufficient to impart the desired degree of water-repellency, the resulting product tends to degenerate too slowly in water and causes plugging of toilets and drains.

DESCRIPTION OF PRIOR ART

U.S. Pat. No. 3,089,493 is representative of both of the features which have characterized the prior art. The patent discloses a partially-disposable colostomy bag which consists of an outer reusable bag or liner made from rubber or other waterproof material and an inner, disposable bag which is made of paper coated on the inner side with a waterproofing material such as lacquer. Correspondingly, this invention presents both of the drawbacks which have characterized the prior art. The outer rubber liner cannot be disposed of in a toilet, for example; and the inner liner requires so thick a coating of lacquer to insure uniform waterproofing that it degenerates slowly in water and can cause plugging of drain pipes.

Other patents disclose a variety of processes which involve only the second approach of coating or impregnating. For instance, U.S. Pat. No. 3,498,527 teaches that paper board containers for liquids can be waterproofed by application of a waterproofing coating such as wax or polyethylene, and a similar method is shown in U.S. Pat. No. 2,708,645 for waterproofing paper drinking cups and in U.S. Pat. No. 3,212,697 for paper grocery sacks. In U.S. Pat. No. 3,597,313, temporary wet strength is imparted to paper by coating it with a polymeric alcohol-polymeric aldehyde reaction product.

Coating processes, by themselves, have been used to produce disposable articles of sanitary clothing. In U.S. Pat. No. 3,078,849, a disposable sanitary napkin is disclosed which consists of an adsorbent layer having a liquid-repellent backing of polyvinyl alcohol or similar material capable of initially repelling water but eventually solubilizing. The degree of water-repellency, therefore the lifetime of the napkin, is controlled by varying the thickness of the backing. Because the necessary life of the napkin cannot be predicted by manufacturer or user, the backing must be sufficiently thick to take account of all normal contingencies. U.S. Pat. No. 3,542,028 is directed to a flushable sanitary napkin consisting of a cellulosic sheet treated with a fluoropolymer coating. U.S. Pat. No. 3,559,650 teaches the preparation of a sanitary napkin having two flush-disposable sides separated by a waterproof film too thin to support itself once both faces of the napkin have disintegrated upon disposal.

Analogous to the process of coating a surface with a waterproofing substance is the concept of reacting a surface with another material so as to form a reaction product on the surface which has water-repellent properties. For example, U.S. Pat. Nos. 2,130,212 and 3,137,540 teach that materials such as polymeric alcohols may be reacted with other materials to increase their water-repellent properties. The latter patent teaches treating polyvinyl alcohol articles with an aqueous emulsion of an aldehyde to impart water-repellency thereto. U.S. Pat. No. 3,626,943 teaches that disposable diapers can be made from polyvinyl alcohol and waterproofed on one side by reaction with formaldehyde. These reaction-type coating processes suffer from many of the same drawbacks heretofore mentioned for regular coating processes. Moreover, these processes are carried out in the aqueous phase which is cumbersome, time-consuming, and requires relatively large quantities of reagents. Although most of the processes which employ some form of in situ chemical reaction to produce a water-repellent surface are carried out in the liquid phase, some vapor phase treatments are taught by U.S. Pat. Nos. 2,306,222; 2,961,388; and 3,017,290. However, this group of patents is not directed to resolving the conflicting goals of obtaining a product which is water-repellent in use but water-dispersable at the time of disposal. In fact, U.S. Pat. No. 2,306,222 states specifically that paper treated according to the invention will not disintegrate in water. Therefore, none of the prior art teaches a wholly satisfactory process for making disposable water-repellent cellulose articles.

RELATED PATENTS

U.S. Pat. No. 3,934,587, by the same inventor as this application, discloses a waterproofing process which overcomes many of the shortcomings of the prior art. In particular, the patent discloses a process for treating a polymeric sheet or film containing reactable hydroxyl or amine groups with a vapor phase mixture of acid chloride and aldehyde. The resulting product is water-repellent along the treated side and water-permeable along the opposite, untreated side. In the aforementioned patent, the degree of water-repellency of the treated side of the polymeric sheet is controlled, principally, by adjusting the proportions of acid chloride and aldehyde in the vapor phase mixture. Generally, the patent teaches that a higher proportion of acid chloride to aldehyde in the vapor phase mixture results in a comparatively soft treated surface of low durability. Utilizing a vapor of acid chloride alone is said to result in an especially soft surface of relatively low water-repellency. Thus, a vapor mixture containing at least about 10% aldehyde is considered necessary to obtain a satisfactory treatment. A major drawback to the process disclosed in U.S. Pat. No. 3,934,587, however, is the high cost of the aliphatic aldehydes as well as their susceptibility to oxidation, decomposition and polymerization in storage. In treating a very inexpensive raw material such as cellulose, even relatively small differences in processing costs can make significant commercial differences.

FIELD OF THE INVENTION

The present invention is directed to the surprising discovery that sheets, pads or cloth of cellulose exposed along one or more sides or edges to acid chloride vapors for very short reaction times of about 1 to 15 seconds are rendered highly water-repellent. Depending on the length of exposure and the characteristics of the cellulose being treated, a one-sided water-repellent effect can be achieved producing a product suitable for disposable containers, articles of sanitary clothing and the like. Alternatively, pads or cloth of cellulose can be treated along one side and two or more edges or along both sides and two or more edges to produce products suitable for bandaging and related applications. The selection of cellulose and treatment parameters will vary depending on the desired end-use of the treated cellulose as hereinafter described.

OBJECTS OF THE INVENTION

Accordingly, the principal and specific object of this invention is to provide a process for treating cellulose with vapors of an aliphatic acid chloride to obtain a water-repellent surface.

Another object of this invention is to provide a treated cellulose sheet or pad uniquely characterized by the properties or capabilities both of being one-side water-repellent and capable of absorbing and storing aqueous fluids during use and of being readily disintegrated when disposed of in an aqueous environment.

Another object of the present invention is to provide treated cellulose sheet or cloth which is water-repellent on both sides.

Still another object of the present invention is to provide a process and apparatus for producing the treated cellulose sheets, pads or cloth of this invention.

A further object of the present invention is to provide articles suitable for sanitary clothing, bandaging and the like whereby they meet the ideal requirements of one-time use and of quick and easy disposal.

Further objects and advantages will become apparent as the following description proceeds.

DESCRIPTION OF PREFERRED EMBODIMENT

Figure 1:
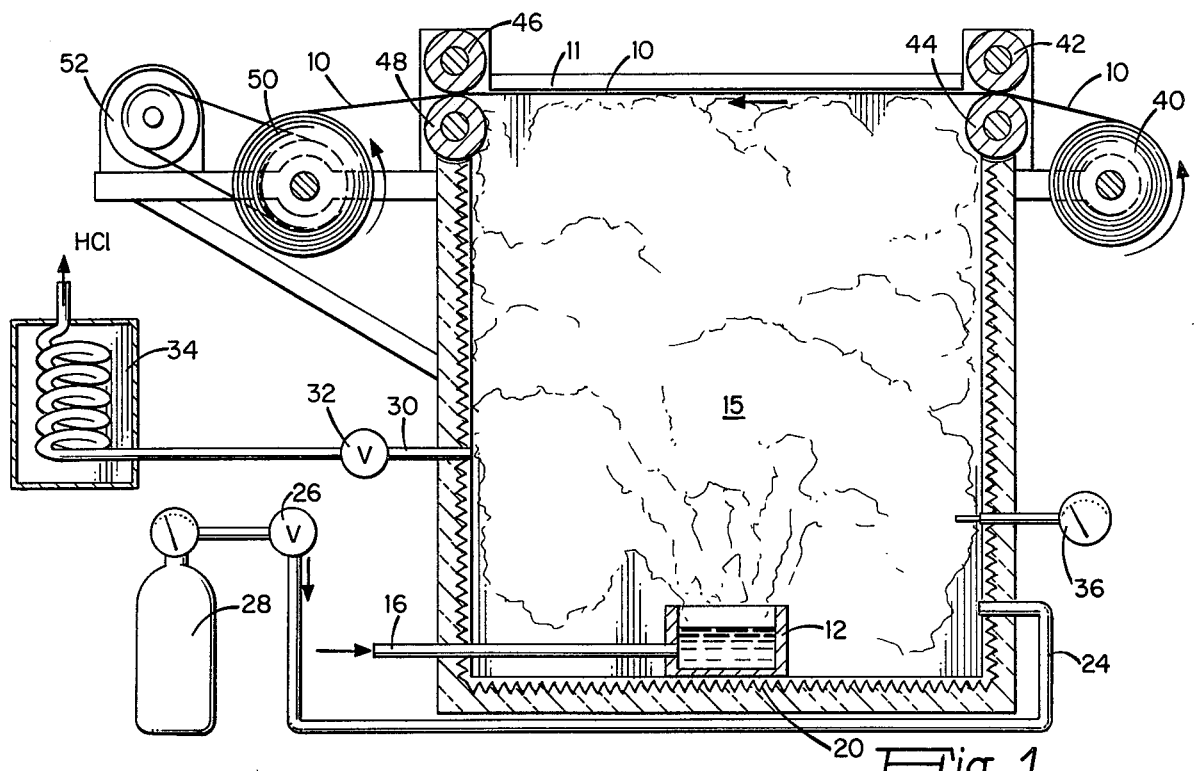
FIG. 1 is a cutaway view of the apparatus for carrying out the process of the present invention.

Referring more particularly to FIG. 1 by characters of reference, the principal element of the apparatus for practicing the present invention is an open-top, insulated rectangular reaction chamber defining an enclosed zone 15 having a liquid-holding container 12 placed along the bottom of the inside of said chamber. Container 12 is supplied with liquid-phase acid chloride, as hereinafter described, from an external source by pipe 16. Alternatively, acid chloride vapors may be supplied directly to zone 15 from any convenient external source such as the vapors which are distilled as part of the ordinary acid chloride purification process. The reaction chamber is heated along all sides by heat source 20 sufficiently to obtain the desired vapor pressure of acid chloride in the chamber and also is insulated to prevent condensation of the vapors on the interior walls. It will be appreciated that any suitable heating means may be employed such as an electrical resistance coil or merely by placing the entire reaction chamber in an oven.

In the preferred practice of the present invention, acid chloride is fed to container 12, and sufficient heat is applied by heat source 20 to vaporize the required amount of acid chloride thereby creating a vapor having the desired vapor pressure in zone 15 of the reaction chamber. In general, it has been found that a partial vapor pressure of acid chloride on the order of 10–100 mm. of mercury is sufficient to obtain good water-repellency in reaction times of 1–15 seconds. Furthermore, it has been found that temperature is not a critical parameter except that the temperature in zone 15 must be sufficiently high to maintain the desired vapor pressure of acid chloride. This, of course, will vary for different acid chlorides depending on the hydrocarbon chain length. Also, because reaction temperature is not critical, the cellulose sheet, pad or cloth need not be preheated or otherwise pretreated in any special way.

Materials suitable for treatment by the process of this invention include various forms of cellulose, such as cotton fibers, plant fibers such as flax, wood fibers, regenerated cellulose (rayon and cellophane), partially alkylated cellulose (cellulose ethers), partially esterified cellulose (acetate rayon), and other modified cellulose materials which have a substantial portion of their hydroxyl groups available for reaction. Also included are synthetic polymers or copolymers which are insoluble in water, but are hydrophillic and reactive because they contain substantial numbers of hydroxyl (—OH), sulfhydryl (—SH) and/or amine (—NH) groups. As used herein, the term "cellulose" is meant to include all of these materials and others of similar chemical structure and having similar properties.

The acid chlorides suitable for the practice of the present invention are those having the general formula

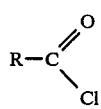

wherein R is selected from straight-chain, branched-chain, or cyclic aliphatic hydrocarbon radicals having from about 6 to about 20 carbon atoms. In general, it has been found that acid chlorides containing fewer than about 6 carbon atoms do not produce satisfactory water-repellency. On the other hand, while water-repellency generally improves with increasing chain lengths, the temperatures required to obtain suitable vapor pressures of acid chlorides containing more than about 20 carbon atoms are so high that most forms of cellulose begin to deteriorate. Unlike polyvinyl alcohol, however, treatment of cellulose with the longer chain acid chlorides does not result in a soft or tacky surface. Accordingly, acid chlorides having from 10–16 carbon atoms in the chain are preferred for this invention. Exemplary of compounds wherein R is selected from aliphatic hydrocarbon radicals are caprylyl chloride (octanoyl chloride), decanoyl chloride, lauroyl chloride, palmitoyl chloride and stearoyl chloride. Exemplary of compounds wherein R is selected from cyclic aliphatic hydrocarbon radicals is cyclohexanecarboxylic acid chloride. Generally, however, straight-chain acyclic aliphatic acid chlorides are preferred for this invention because they are usually cheaper and more readily available and also because the branched-chain and cyclic hydrocarbon radicals are not easily biodegradable. In some instances it may be desirable to employ a mixture of two or more acid chlorides, and such embodiments are within the scope of the present invention. Also, acid bromides and acid iodides react in similar ways to the acid chlorides and may be substituted therefor. However, because the bromides and iodides are generally more expensive and less readily available, the equivalent acid chlorides are usually preferred. For the practice of the present invention, ordinary commercial grade acid chlorides have been found wholly suitable, the only necessary precaution being to prevent exposure of the easily hydrolyzable acid chlorides to moisture.

The reaction chamber is also furnished with a gas inlet 24 and a valve 26 for adding diluent gas to the chamber, and similarly is furnished with an outlet 30, valve 32, and a reflux condenser 34 maintained at about 10° C., which allows reaction by-product HCl (gas) to escape, but condenses most of the acid chloride vapors and returns them to the reaction chamber. The by-product gas stream may be treated, for example by bubbling it into a container of an aqueous alkaline solution to remove HCl and any excess acid chloride prior to exhausting it to the atmosphere. The preferred diluent gas is nitrogen which is inexpensive and does not react with acid chloride vapors, whereas the oxygen in air could lead to oxidation of the acid chloride. Nitrogen may be conveniently supplied by a cylinder 28 of the compressed gas. It is preferred to continuously add a stream of dry nitrogen or other inert diluent gas to reaction chamber 15 to sweep out the by-product HCl and prevent accumulations of HCl which might attack the cellulose. Ordinarily the process of the present invention is carried out at or about atmospheric pressure, i.e. about one atmosphere or 14.7 psia. In the preferred practice of the present invention, the reaction chamber is also furnished with an external thermometer 36 to record the internal conditions of the reaction chamber.

Affixed to one wall of the rectangular reaction chamber by suitable supporting means is a spool or roll 40 of the sheet, pad or cloth 10 of cellulose employed in the present invention. "Sheet" is meant to include any relatively continuous thin layer of cellulose such as paper or cardboard. "Cloth" is mean to include relatively open woven cellulose fabrics such as cotton gauze as well as more closely woven cellulose fabrics. "Pad" is meant to include loose cellulose wadding such as paper fibers, cotton and the like, covered at least in part by a supporting cellulose sheet or cloth. The sheet or cloth may be of any suitable thickness such as about 1 mm. but must be thick enough to be relatively self-supporting and thin enough to be reasonably flexible. Within these limits, the thickness will be selected depending on how closely woven the cellulose is, the desired end-use of the product, and the most efficient treatment time. The apparatus may, however, be adapted to accommodate flat sheets of materials which are too stiff or brittle to be rolled on a spool or, as described below, irregularly shaped cellulose surfaces.

Figure 2:
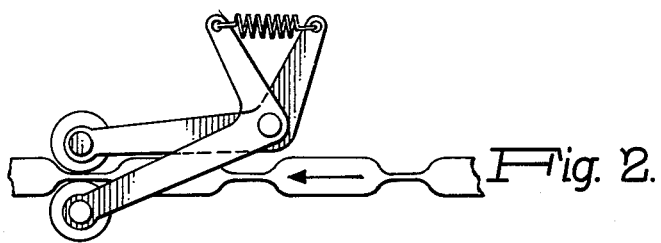
FIG. 2 is a blow-up schematic view of the feeding (or exit) rollers through which the continuous length of cellulose to be treated enters or leaves the reaction chamber.

The cellulose pad may be a continuous length of supported wadding or, alternatively, as illustrated in FIG. 2, the continuous length of support material may enclose wadding only at discrete and approximately evenly-spaced locations along its length thereby defining individual pads suitable for bandaging, sanitary napkins, etc.

No special preparation of the material is necessary in practicing this invention except that the surface to be treated should be clean and free of dirt and excess moisture. In most cases, normally air-dried material which contains a few percent adsorbed moisture may be used. In some cases, material can be dried prior to treatment (e.g. at 110° C. for a few minutes) to remove most of the adsorbed moisture. Little if any effect of this drying on water-repellency has been noted except for a few particularly hygroscopic materials which had improved water-repellency when pre-dried.

Figure 3:
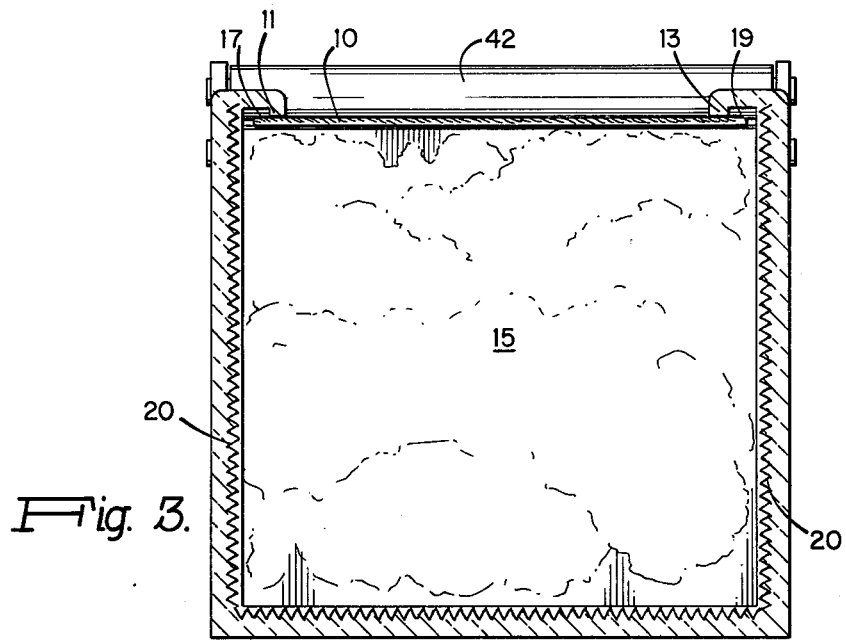
FIG. 3 is a side view taken along a section through the apparatus shown in FIG. 1.
Figure 4:
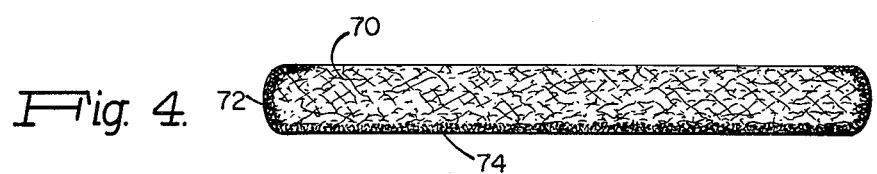
FIGS. 4–6 are cross-sections of composite materials for making sanitary napkins, bandages and the like according to the present invention.

The spool or roll 40 and the sheet or pad 10 of cellulosic material wound on the spool are slightly less wide than the reaction chamber so that the sheet or pad can pass between the specially-formed lips running lengthwise along both sides of the chamber. These lips 11 and 13, illustrated more clearly in FIG. 3, are seen to comprise narrow and slightly overhanging ledges projecting from the two length-wise sides of the reaction chamber and having slits at the points where they would otherwise be joined to the width-wise sidewalls of the chamber. By maintaining close tolerances between the overhanging portions of the lips and the sheet or pad 10 of cellulosic material as it is passed through the slits and under the overhanging portion of the lips, it is possible to provide a sufficient seal at the open top of the reaction chamber. The slight overhanging portions of the lips 11 and 13 create recessed cavities 17 and 19 communicating with the interior 15 of the reaction chamber and filled with acid chloride vapor. Thus, this arrangement facilitates treating not only the underside of the sheet or pad 10 but also, if desired, the two side edges and the adjoining fringe area along the upperside of the sheet or pad as illustrated in FIG. 4.

Referring again to FIG. 1, coming off spool 40, the sheet or pad 10 is passed between fixed rollers 42, 44 and then through the slits as described above and over the top of the reaction chamber. The acid chloride vapor inside the chamber reacts with the exposed cellulosic surface to form a water-repellent material. At the opposite wall of the chamber, the treated sheet or pad is removed from the chamber by passing through the second set of slits defined by lips 11, 13 and between another set of rollers 46, 48 and wound on a take-up spool 50 driven by variable speed motor 52. Sufficient tension is maintained between rollers 42, 44 and rollers 46, 48 so that a tight seal is formed between the cellulose sheet and the overhanging lips of the reaction chamber. Such a design has been found to work quite well in maintaining the vapors inside the chamber when operated at or about atmospheric pressure. Certain design changes would be required, however, to operate the reaction chamber at pressures higher or lower than atmospheric pressure.

Where an irregularly-shaped pad, as previously described, is to be treated according to this invention, fixed inlet rollers 42, 44 and outlet rollers 46, 48 can be replaced with movable rollers held together by spring tension as illustrated in FIG. 2 or by any equivalent means. This arrangement readily accommodates a pad of varying thickness while minimizing the loss of acid chloride vapor. Another way to treat a pad on all sides except one to form a structure as illustrated in FIG. 4 is to bring the pad on a flat plate or conveyor belt into an oven containing the vapors of an acid chloride. The unexposed side of the pad remains absorbent because it is protected from treatment with the vapors by the plate or belt while the other surfaces are all treated to become water-repellent.

Figure 7:
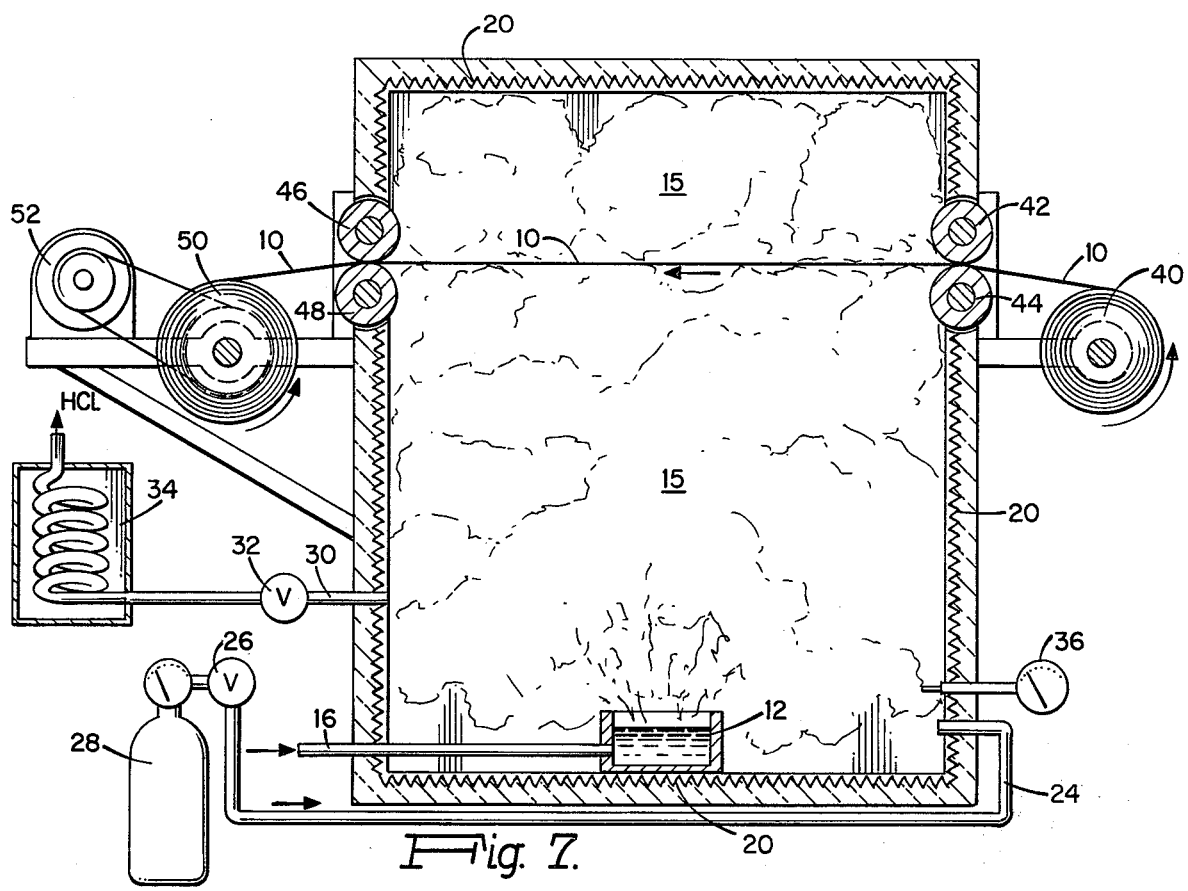
FIG. 7 shows an alternative embodiment for a two-side treating process.

In treating a cellulose sheet or cloth and, sometimes, a pad, it is often desirable to treat both sides or surfaces simultaneously. This can be accomplished by modifying the apparatus of FIG. 1 as shown in FIG. 7. The top of the chamber in FIG. 7 is closed and the sheet, pad or cloth is introduced into the interior of the chamber instead of along the top side. In this embodiment, the width of the chamber should be somewhat greater than the width of the material being treated to insure full circulation of acid chloride vapor to the upper portion of the chamber interior. This latter feature, of course, is not important in treating a cellulose tissue or cloth of fairly open construction which does not impede the flow of vapors through the interior of the chamber.

The reaction time, that is the length of time for which it is necessary to expose the cellulosic sheet, pad or cloth, to the acid chloride vapors in the reaction chamber, varies according to the specific materials being employed, the reaction conditions, and the end-use of the treated product. Typically, however, the required time of exposure is about 1 to 15 seconds. The concentration of acid chloride vapor in the reaction chamber, and the consequent rate of reaction, may be varied to some extent by changing the temperature to obtain a desired rate of reaction. The maximum operable temperature, however, is that at which the cellulose being treated begins to decompose, normally about 200° C. The exposure time for a reaction chamber of a given length is easily adjusted by changing the speed of the motor 52 driving take-up spool 50. It is preferred to adjust the speed so that the surface treatment to whatever extent is desired is completed by the time the material has traveled the length of the reaction chamber. The two interior rollers 44 and 48 will tend to remain clean of reactant because they are heated to approximately the same temperature as the interior of the reaction chamber. Thus, these vapors will not generally condense on the internal metal parts of the reaction chamber. The treated sheet, pad or cloth collected on spool 50 may then be used for a variety of novel applications as hereinafter described.

One of the principal advantages of the method of the present invention over the process disclosed in U.S. Pat. No. 3,934,587 is that the instant treatment process does not require the presence of long-chain aldehydes. As previously discussed the essence of the present invention is the surprising discovery that satisfactory water-repellent characteristics can be imparted to cellulose surfaces by vapor treatment with long-chain acid chlorides even in the absence of aldehydes. This is commercially significant because the long-chain aldehydes are difficult to prepare, purify, and store and, accordingly, are from 10 to as much as 1,000 times as costly as the corresponding long-chain acid chlorides of comparable purity. In addition, the use of only a single reactant in the present invention, instead of the two reactants used in U.S. Pat. No. 3,934,587 considerably simplifies the apparatus design and control.

By "water-repellent" is meant the ability of a surface to substantially impede the passage of liquid water for an indeterminately long period of time. Alternatively, imparting "water-repellent" characteristics to cellulose may be considered as changing the normally hydrophilic characteristics of most cellulose materials to being hydrophobic instead. Because of the nature of cellulose as a porous mass of fibers, imparting water-repellent characteristics to cellulose surfaces is significantly different from water-proofing a substantially continuous and non-porous surface such as a sheet of polyvinyl alcohol. A discussion of the physical and chemical aspects of water penetration of porous fibers appears in the following publications: J. E. Foote, "A Method for the Measurement of the Angle of Contact Formed Between a Liquid Surface and a Fiber, and the Application of This and Swelling Data to Pore Diameter Measurements", *Paper Trade Journal,* Vol. 109, No. 14, pp. 40–48 (Oct. 5, 1939); and, "Penetration of Papers by Liquids and Solutions", *Paper Trade Journal,* Vol. 110, No. 4, pp. 44–50 (Jan. 25, 1940). Because of the porous fibrous nature of cellulose, it is difficult to render even a very closely woven cellulose entirely "waterproof" with a surface treatment such as that described herein. Under sufficient pressure, the water-repellency characteristics can be overcome and droplets of liquid water can be "squeezed" through the pores between the cellulose fibers. The smaller the average pore diameter of the sheet, and the thicker the sheet, the greater is the water pressure which is required to force liquid through the treated sheet, however.

The degree of water-repellency can thus be controlled, by selection of the pore size and the thickness of the cellulose to be treated and also by varying the treatment conditions, in particular the acid chloride selected, the vapor pressure (concentration) of acid chloride in the reaction chamber and the duration of the exposure. In general, longer chain acid chlorides give greater water-repellency, other factors such as depth of cellulose treated being equal. By increasing the vapor pressure of acid chloride for example to about one-half atmosphere partial pressure or, alternatively, increasing the exposure time, acid chloride vapors can penetrate more deeply into the cellulose being treated with the net result that again improved water-repellent characteristics are exhibited. It appears that the reaction of acid chloride and cellulose is diffusion controlled. Therefore, while the outer exposed surface of a fairly tightly-woven cellulose reacts almost instantaneously, sub-surface layers take longer to be treated depending on the distance from the surface exposed to acid chloride vapors. It has been found that the thickness of cellulose treated is proportional to the square root of the exposure time. The constant in the proportionality equation will, of course, vary depending on the type of cellulose being treated, especially the size of the interstices between strands of cellulose, and, to a lesser extent, on the treatment conditions. An important implication of this discovery that the reaction is diffusion-controlled, is that an outer layer of a cellulose pad can be made water-repellent without reducing the absorptive capacity of the inner portion of the pad.

An important feature of cellulose for purposes of this invention is that the cellulose strands are typically already sufficiently tightly bound together that no further cross-linking is required for water-repellency once the surface of the strands is treated according to this invention. The treatment process of this invention is believed to be represented by the following general reaction based on what is believed to be the basic cellulose unit—$(C_6H_{10}O_5)_n$:

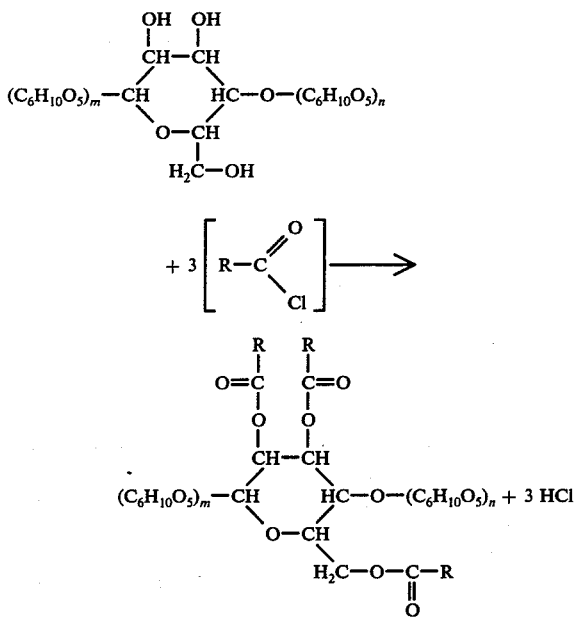

In the above reaction, one or more of the three free hydroxyl groups in each basic cellulose "unit" reacts with acid chloride to form a highly water-repellant aliphatic ester and hydrogen chloride. The structure of cellulose is such that no further treatment of its surface is required for imparting excellent water-repellent characteristics.

Although a similar initial reaction occurs between polyvinyl alcohol (PVA) and acid chloride, the absence of cross-linking in the PVA structure permits water droplets to penetrate the treated PVA surface. Once a water droplet penetrates the treated surface, it is readily absorbed into the untreated water-soluble PVA below the surface causing swelling and disintegration which, in turn, permits additional water to enter and quickly destroys the water-repellent characteristics. This effect is similar to that encountered with untreated PVA as disclosed in U.S. Pat. No. 3,078,849, which was earlier discussed. In essence, this is a "timed" water-repellency which can "give out" quickly and unexpectedly in the presence of moisture. Clearly this is not a desirable quality for such articles as bandages, diapers and sanitary napkins which cannot always be conveniently replaced. It is for this reason that U.S. Pat. No. 3,934,587 requires the use of a mixture of acid chloride and aldehyde vapors for waterproofing polyvinyl alcohol. As described in that patent, in the presence of aldehyde and hydrogen chloride catalyst, the aliphatic esters resulting from the initial reaction of free hydroxyl groups and acid chloride are further reacted and cross-linked to form highly water-insoluble aliphatic acetals.

By contrast, the treatment of the present invention results in cellulose surfaces which are permanently water-repellent without the use of aldehydes. While it is possible to apply sufficient pressure to force a droplet of water through the interstices of the treated cellulose surface of this invention and into the interior portion of the sheet or pad, the treated surface itself remains substantially unaffected. There is little or no swelling of the treated surface fibers, no noticeable disintegration, and the surface remains substantially dry to the touch even while considerable quantities of water are being absorbed into the untreated interior portions of the sheet or pad. These properties make the products of this invention especially suitable for use in such articles as diapers, sanitary napkins, and "no-stick" bandages where it is desirable to draw-off liquids from the surface and contain them for indeterminately long periods of time while retaining a substantially dry water-repellent surface.

The vapor phase treatment is also an important aspect of this invention. Although this invention is not in all cases limited to one-sided water-repellent treatment, in those applications where it is desirable, the vapor phase process of this invention is the best means of achieving it. Vapor phase treatment also avoids the problems of puckering and wrinkling of paper materials which have been subjected to liquid phase treatments. The vapor phase process results in a much more uniform surface since the reactants can reach even small pores and cracks in the surface of the cellulosic material. From a mechanical point of view, the vapor phase process is more easily carried out than liquid phase treatment, and there is less opportunity for clogging of the apparatus. The reaction time is much shorter in this vapor-phase process than in prior art liquid phase processes, and this speed makes it economically possible to treat even low-cost products. The lack of a liquid phase solvent also allows the HCl by-product to diffuse away rapidly before it has a chance to hydrolyze or degrade the cellulose. There is no need for the costly and time-consuming drying steps employed in liquid processes. There is no waste of raw materials nor any need for expensive, poisonous and/or flammable liquid solvents.

Another advantage of the present invention as compared to prior art processes is that the water-repellent products according to the present invention are fully biodegradeable and will not cause long-term damage to the environment. Clearly, this is another important factor in the ready-disposability of articles made from the treated cellulose of this invention.

This invention does not require spraying PVA on a cellulose surface thereby avoiding an additional step and the extra drying time. Still another advantage of this invention is that no petrochemicals, not even PVA, are required because the cellulose and the acid chlorides are derived naturally, acid chlorides being typically produced from coconut oil or the rendering of animal fats. Because this invention only treats the surfaces of the individual cellulose fibers and does not fill in the pores between them, only very small amounts of acid chloride are used. There are no critical controls or tolerances so that automation of this process can easily be accomplished.

Although the benefits and advantages of the present invention as set forth above as compared to prior art materials and processes for waterproofing are substantial in and of themselves, only in the consideration of actual applications of the present invention can these be fully appreciated. The material and process of the present invention are useful in all applications requiring a surface which is water-repellent or an indefinitely long period of time but is water-disposable after use. Sanitary napkins and diapers for children and other persons who are incontinent either because of old age or physical disability are one general type of article for which the present invention is ideally suited.

Referring now to FIG. 4, what is illustrated is a cross-section of an absorbent cellulose pad which has been one-side treated according to the present invention. The pad consists of an inner cellulose wadding portion 70 of paper fibers, cotton, or the like surrounded by an outer tissue-like cellulose portion 72 of sufficient strength to hold the wadding portion of the pad together during the treatment process. The shaded portion of the pad 74 represents the treated, water-repellent layer which includes both the outer tissue covering along the bottom and two sides as well as the adjacent layer of cellulose wadding. A pad of this general type is especially suited to such applications as sanitary napkins or diapers whereby the upperside untreated surface is placed along the skin. The pad thus used is capable of absorbing and containing large quantities of liquids while remaining dry along the outer side of treated portion 74. While layer 74 is only water-repellent and not totally waterproof, only by squeezing a pad which is relatively saturated with liquid is it possible to force liquid through the treated layer. In contrast to polyvinyl alcohol surfaces, layer 74 will not swell or dissolve or otherwise lose its water-repellent characteristics over time. Furthermore, also in contrast to polyvinyl alcohol surfaces, layer 74 is readily water vapor permeable. Thus, the liquids contained in pad 70 will gradually evaporate thereby regenerating the absorptive capacity of the pad. Consequently, where the rate of liquid discharge is not too great, such as with sanitary napkins, or else discharge is periodic, such as with diapers, the life of pads prepared according to this invention is determined solely by user convenience and hygienic considerations. On the other hand, when such a pad is disposed of in an aqueous environment, the untreated portion 70 readily disintegrates and treated portion 74 readily collapses without the support of the pad 70. It should be noted that pads as illustrated in FIG. 4 could not be treated according to prior art liquid-phase processes because the wadding would absorb the treatment solution into the entire pad, rather than just the surface, thereby destroying the absorbency of the interior.

Figure 5:
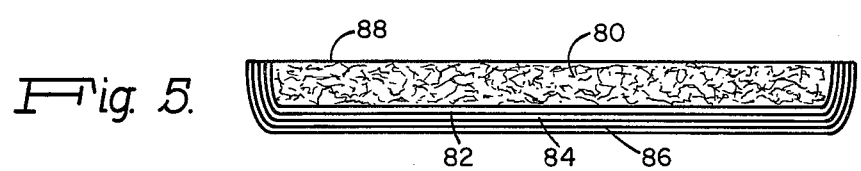

A second type of article suited for the products of this invention is illustrated in FIG. 5. This type of article is also useful for sanitary napkins and diapers but is especially suited to bandaging applications. FIG. 5 illustrates the cross-section of an absorbent pad 80 of cellulose wadding or any comparable natural or synthetic material covered along one side and two edges with successive layers 82, 84 and 86 of treated cellulose and completely surrounded by a final layer 88 of treated cellulose. Layers 82, 84, 86 and 88 may be either a one-side treated or both-side treated sheet or cloth of cellulose, such as very thin tissue paper, or cotton gauze treated in accordance with this invention. If the sheet or cloth has been one-side treated, the treated surface of each of layers 82, 84, 86 and 88 should be the upper or body-facing surface. The layers may be formed by merely cutting the treated sheet or cloth into portions of suitable length and fashioning them around the pad secured by suitable adhesive means or the like or by folding a single length of treated sheet back on itself several times and wrapping the last layer or two around the entire pad. The upper surface of one or perhaps two layers of treated cellulose will be the body-facing side in any of the various applications for a pad constructed in this manner.

There are several advantages to this type of construction. First, and primarily, only a thin sheet or gauze of cellulose needs to be treated in this embodiment rather than a pre-formed pad. This means that the process can be run much more rapidly because it is not necessary that the exposure time be long enough for acid chloride vapors to diffuse into the wadding of the pad as required for the embodiment illustrated in FIG. 4. Also, the apparatus for treating very thin sheets is somewhat less complicated than that required for irregularly-shaped cellulose pads. By placing a very thin layer of treated cellulose along the upper body-facing surface of the pad between the body and absorbent interior wadding, liquid is drawn away from the water-repellent surface layer thereby effecting a non-stick characteristic which is desirable for bandaging. It will be apparent that to achieve this effect requires the use of either a treated cellulose cloth (i.e., relatively loosely woven fabric such as cotton gauze) or a thin treated tissue paper or nonwoven rayon, so that liquid penetration into the absorbent interior of the pad is not unduly impeded. At the same time, the multiple underside layers of treated cellulose will effectively prevent any leakage of fluid under ordinary conditions of use. A further advantage of this embodiment is that the interior absorbent wadding 80 need not be constituted of cellulose but rather may consist of any comparably absorbent loosely structured material, natural or synthetic.

Figure 6:

FIG. 6 illustrates an embodiment of a pad similar to that shown in FIG. 5 where the various layers are formed by folding a sheet or web of treated cellulose over and around an absorbent pad so as to form multiple layers along one side and the edges but only a single layer across the opposite, body-facing side. This embodiment is also especially well-suited for bandaging applications. In fact, because the treatment process of this invention can be carried out at the usual dry sterilization temperatures of 160° to 180° C., treatment and sterilization of these bandaging materials can be carried out simultaneously.

In addition to the illustrated embodiments, there are many other variations and applications for products produced in accordance with this invention. For example, thin porous cellulose material treated according to this invention may be used as a wound releasing (non-stick) body-facing layer for any conventional type of bandage or dressing. They may also be used to cover the outsides of surgical gowns and related clothing to maintain a substantially clean and dry surface during use.

Heavier grades of paper and cardboard may be one-side treated according to this invention for fashioning disposable cups, paper bags and other containers which are desirably water-repellent along at least one surface while in use. Similarly, it will be appreciated that additional physical strength and water-repellency can be obtained by placing two or more treated paper sheets together. The waterproof material produced according to this invention is not harmed by heat up to the temperature at which cellulose itself begins to decompose (e.g.

about 200° C. for short periods, or 150° C. for longer times). Thus this new material can be used to contain hot liquids (e.g. coffee) which would melt the wax which is often used to waterproof cups, while being less expensive to produce than heat-resistance plastic cups.

It will be apparent that the selection of cellulose to be treated, of acid chloride reagent, of reaction temperature (or vapor pressure), and of exposure time are process parameters which can be optimized by routine experimentation conducted by one of ordinary skill in the art in order to suit any particular application for the final product. For example, in the one-side treatment of a sanitary pad as illustrated in FIG. 4, some routine experimentation may be required to determine what exposure time yields satisfactory water-repellent characteristics while at the same time minimizing the amount of interior wadding which is reacted and not available for absorbing liquid.

The following examples will further illustrate this invention and the advantages thereof.

EXAMPLE 1

Sheets of cellulose in the form of very thin tissue paper were treated with vapors of the following aliphatic acid chlorides of general formula $CH_3(CH_2)_nCOCl$:

Octanoyl chloride ($n = 6$)
decanoyl chloride ($n = 8$)
lauroyl chloride ($n = 10$)
myristoyl chloride ($n = 12$)
palmitoyl chloride ($n = 14$)
stearoyl chloride ($n = 16$)

Treatment temperatures were adjusted so as to maintain vapor pressures of acid chloride between about 10–20 mm. Hg in each case, higher temperatures being required for the longer chain acid chlorides. Treatment times varied between 1 and 60 seconds.

The resulting sheets of cellulose were tested for water-repellency in two ways:

(1) Individual fibers removed from each treated sheet and placed on a water surface simply floated on the surface without penetrating into the water. By contrast, the original, unreacted cellulose fibers became wet and sank into the water within a few seconds.

(2) Small drops of water were placed on the surface of each treated cellulose sheet. The droplets assumed essentially spherical form, and dit not penetrate significantly into the sheet. The untreated sheets, by contrast immediately absorbed the droplets. When shorter-chain acid chlorides were used ($n < 6$), the water-repellency was not so complete, and water drops were usually absorbed slowly by paper treated with the short-chain acid chlorides.

Each of these tests indicates that a highly hydrophobic surface has been formed on the cellulose fibers by the treatment in accordance with this invention.

EXAMPLE 2

This set of tests was conducted to determine the effectiveness of the process of this invention in rendering thicker layers of material water-repellent. The thicker layers comprised in some cases multiple layers of tissue paper and in other cases absorbent pads of paper or cotton fibers.

In all cases, the side exposed to acid chloride vapor developed a high degree of hydrophobic character. The dividing line between the part of the material which was esterified and the unreacted part appeared to be quite sharp. It could be clearly measured, for example, by placing a dilute solution of a water-soluble dye on the unreacted side. The solution penetrated into the unreacted part of the pad, but stopped abruptly upon reaching the reacted portion. This is evidence of the extremely uniform treatment achieved by the vapor process of this invention. A reaction time of 5 to 15 seconds was generally sufficient to penetrate and esterify several layers of paper, but the exact rates depend considerably on the porosity of the paper. These thicker unreacted layers are highly water-repellent and, even when the unreacted portion of the cellulose is saturated with water or dye solution, penetration does not occur into the reacted layers. After standing for a period of several hours, the water evaporated rather than filtering through the reacted layers. Thus, acid chloride alone is capable of producing a satisfactory degree of water-repellency with cellulose.

Attempts to remove or dissolve the esterified material with alcohol, acetone, ether, carbon tetrachloride or soap solution failed to change the material or to alter its hydrophobic properties. Some swelling of the cellulose fibers was noted, particularly with water. The fibers retain their hydrophobic character even after complete immersion in water, however. Although some water is absorbed, as shown by the fact that the tissue under a water drop increases in size and forms a depression, the tissue does not allow the drop to penetrate.

EXAMPLE 3

This set of tests was conducted to compare the water-repellent characteristics of the products of this invention with those of polyvinyl alcohol sheets treated in a similar manner.

Experiments were carried out to compare directly the waterproofing effects of aliphatic acid chlorides on cellulose and on polyvinyl alcohol films. The same results were found in separate reactions of these types run on different occasions: Satisfactory waterproofing results were obtained with cellulose, but not with polyvinyl alcohol.

In the first series of experiments, lauroyl chloride vapors at 150° C. in a laboratory drying-type oven were used. The lauroyl chloride liquid was placed in a pyrex baking pan on the lower shelf of the oven, and after it warmed up, the sample sheets were placed for 10 seconds on the upper shelf. The cellulose sheets comprised filter paper, and the polyvinyl alcohol was in the form of plasticized sheets. The filter paper was water absorbent before treatment, and the polyvinyl alcohol was water-soluble.

After treatment with the lauroyl chloride vapor for 10 seconds at 150° C., the paper became completely water-repellent. Drops of water rolled along its surface instead of soaking in, and the water did not penetrate the filter paper at all even after several hours, after which it evaporated. In order to test the treatment over a longer period, pieces of the filter paper were floated on a beaker of water, on which they remained without being wet or sinking. The upper paper surface remained dry when observed the next day.

The polyvinyl alcohol sheets treated under the same conditions, however, showed only slight water-repellency. They began to swell as soon as drops of water were placed on their surface, and within a minute, the films under the drops dissolved. This dissolution was only slightly slower than in the case of untreated polyvinyl alcohol films. This test verified that the presence of aldehydes as a cross-linking agent is essential to the waterproofing reaction for polyvinyl alcohol, but is unimportant in cellulose, which has a sufficiently rigid polymeric structure even without the cross-linking by aldehydes.

Similar tests on cellulose and PVA were repeated with myristoyl chloride at 180° C. for 10 seconds. The results were substantially identical to those described above for lauroyl chloride. The only change noted was that the necessarily higher reaction temperature for the longer chain myristoyl chloride caused more softening and curling of the polyvinyl alcohol film.

Further tests were also conducted to determine whether any chemical residues from the treatment process remained on the treated cellulose surfaces which might make contact with skin, food, etc. harmful. The tests proved that there were no detectable residues of hydrogen chloride or acid chloride on the treated cellulose surfaces.

Although several embodiments of the present invention have been described and illustrated, it will be apparent to those skilled in the art that various changes and modifications may be made therein without departing from the spirit of the invention or from the scope of the appended claims.

Having described the invention, what is claimed is:

1. An article of manufacture comprising a sheet, pad or cloth of cellulose characterized in that at least one side thereof is water-repellent wherein said water-repellent side consists essentially of the reaction product of the cellulose with an aliphatic acid chloride in the vapor phase, said acid chloride having the general formula

wherein R is selected from straight-chain, branched-chain, or cyclic aliphatic hydrocarbon radicals having from about 6 to about 20 carbon atoms.

2. An article according to claim 1 wherein said reaction is carried out at atmospheric pressure and at a temperature high enough to create a partial vapor pressure of acid chloride of about 10-100 mm. Hg.

3. An article according to claim 2 wherein said acid chloride is lauroyl chloride and the temperature is about 150°-200° C.

4. An article according to claim 2 wherein said acid chloride is myristoyl chloride and the temperature is about 180°-200° C.

5. An article according to claim 2 wherein said acid chloride is palmitoyl chloride and the temperature is about 200° C.

6. An article according to claim 2 wherein the reaction time is about 1-15 seconds.

7. A process for imparting water-repellent characteristics to at least one side of a cellulose sheet, pad or cloth comprising the steps of exposing said at least one side to a vapor phase consisting essentially of aliphatic acid chloride having the general formula R—C(=O)Cl wherein R is selected from straight-chain, branched-chain or cyclic aliphatic hydrocarbon radicals having from about 6 to about 20 carbon atoms.

8. The process of claim 7 wherein said reaction is carried out at atmospheric pressure and at a temperature high enough to create a partial vapor pressure of acid chloride of about 10-100 mm. Hg.

9. The process of claim 8 wherein said acid chloride is lauroyl chloride and the temperature is about 150°-200° C.

10. The process of claim 8 wherein said acid chloride is myristoyl chloride and the temperature is about 180°-200° C.

11. The process of claim 8 wherein said acid chloride is palmitoyl chloride and the temperature is about 200° C.

12. The process of claim 8 wherein the reaction time is about 1-15 seconds.

13. The process of claim 7 wherein the cellulose to be treated comprises a thin paper sheet which is simultaneously treated along both sides.

14. The process of claim 7 wherein the cellulose to be treated comprises a pad which is treated along one side and two edges.

15. The process of claim 7 wherein the cellulose to be treated comprises a cloth or gauze fabric.

16. A disposable article of sanitary clothing comprising an absorbent cellulose pad treated along the side opposite the body-facing side by exposure to a vapor consisting essentially of acid chloride having the general formula

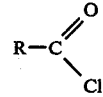

wherein R is selected from straight-chain, branched-chain or cyclic aliphatic hydrocarbon radicals having from about 6 to about 20 carbon atoms.

17. An article according to claim 16 wherein said reaction is carried out at atmospheric pressure and at a temperature high enough to create a partial vapor pressure of acid chloride of about 10-100 mm. Hg.

18. An article according to claim 17 wherein said acid chloride is lauroyl chloride and the temperature is about 150°-200° C.

19. An article according to claim 17 wherein said acid chloride is myristoyl chloride and the temperature is about 180°-200° C.

20. An article according to claim 17 wherein said acid chloride is palmitoyl chloride and the temperature is about 200° C.

21. An article according to claim 17 wherein the reaction time is about 1-15 seconds.

22. A disposable, nonsticking bandaging material or dressing comprising an absorbent pad surrounded by one or more layers of a sheet or cloth of cellulose treated along at least one side thereof by exposure to a vapor consisting essentially of acid chloride having the general formula R—C(=O)Cl wherein R is selected from straight-chain, branched-chain or cyclic aliphatic hydrocarbon radicals having from about 6 to about 20 carbon atoms, whereby a single layer of the treated cellulose covers the absorbent pad along the body-facing side and a plurality of layers covers the opposite side of the pad.

23. The material of claim 22 wherein said reaction is carried out at atmospheric pressure and at a temperature high enough to create a vapor pressure of acid chloride of about 10-100 mm. Hg.

24. The material of claim 23 wherein said acid chloride is lauroyl chloride and the temperature is about 150°-200° C.

25. The material of claim 23 wherein said acid chloride is myristoyl chloride and the temperature is about 180°-200° C.

26. The material of claim 23 wherein said acid chloride is palmitoyl chloride and the temperature is about 200° C.

27. The material of claim 23 wherein the reaction time is about 1-15 seconds.

28. A disposable paper container for containing aqueous liquids comprising cellulosic paper which has been exposed along the side normally coming into contact with aqueous liquids to a vapor phase consisting essentially of acid chloride, said acid chloride having the general formula

wherein R is selected from straight-chain, branched-chain or cyclic aliphatic hydrocarbon radicals having from about 6 to about 20 carbon atoms.

29. An article according to claim 28 wherein said reaction is carried out at atmospheric pressure and at a temperature of about 150°-200° C., and the reaction time is about 1-15 seconds.

* * * * *